(12) United States Patent
Smith

(10) Patent No.: US 6,286,670 B1
(45) Date of Patent: Sep. 11, 2001

(54) METHOD AND APPARATUS FOR MIXING A COMPOUND UTILIZING A GAS PERMEABLE BARRIER

(75) Inventor: Daniel B. Smith, Warsaw, IN (US)

(73) Assignee: Biomet, Inc., Warsaw, IN (US)

( * ) Notice: Subject to any disclaimer, the term of this patent is extended or adjusted under 35 U.S.C. 154(b) by 0 days.

(21) Appl. No.: 09/524,846

(22) Filed: Mar. 14, 2000

(51) Int. Cl.[7] .................................................. B65D 25/08
(52) U.S. Cl. ....................... 206/221; 206/219; 206/524.8
(58) Field of Search .................................. 206/219, 221, 206/524.8; 604/410, 416

(56) References Cited

U.S. PATENT DOCUMENTS

| | | | |
|---|---|---|---|
| 5,333,736 | * 8/1994 | Kawamura | 206/524.8 |
| 5,370,221 | 12/1994 | Magnusson et al. . | |
| 5,398,483 | 3/1995 | Smith et al. . | |
| 5,588,745 | * 12/1996 | Tanaka et al. | 366/130 |
| 5,788,078 | * 8/1998 | Fuss | 206/521 |
| 5,951,160 | 9/1999 | Ronk . | |
| 5,997,544 | 12/1999 | Nies et al. . | |

\* cited by examiner

*Primary Examiner*—David T. Fidei
(74) *Attorney, Agent, or Firm*—Harness, Dickey & Pierce, P.L.C.

(57) ABSTRACT

A container for containing first and second components that are to be mixed with one another. The container includes a divider and a barrier mechanism. The divider isolates a first compartment containing the liquid component from a second compartment for containing the powder. A vacuum source is placed in fluid communication with the second compartment. The vacuum source is of sufficient size and pressure to cause the first component to be drawn through the second component to ensure thorough admixing of the first and second components after the integrity of the divider has been compromised. The barrier mechanism is disposed between the second compartment and the vacuum source and forms a barrier to resist infiltration of the first component but permit the passage of gas into the vacuum source. A method for forming a compound using the container of the present invention is also provided.

33 Claims, 4 Drawing Sheets

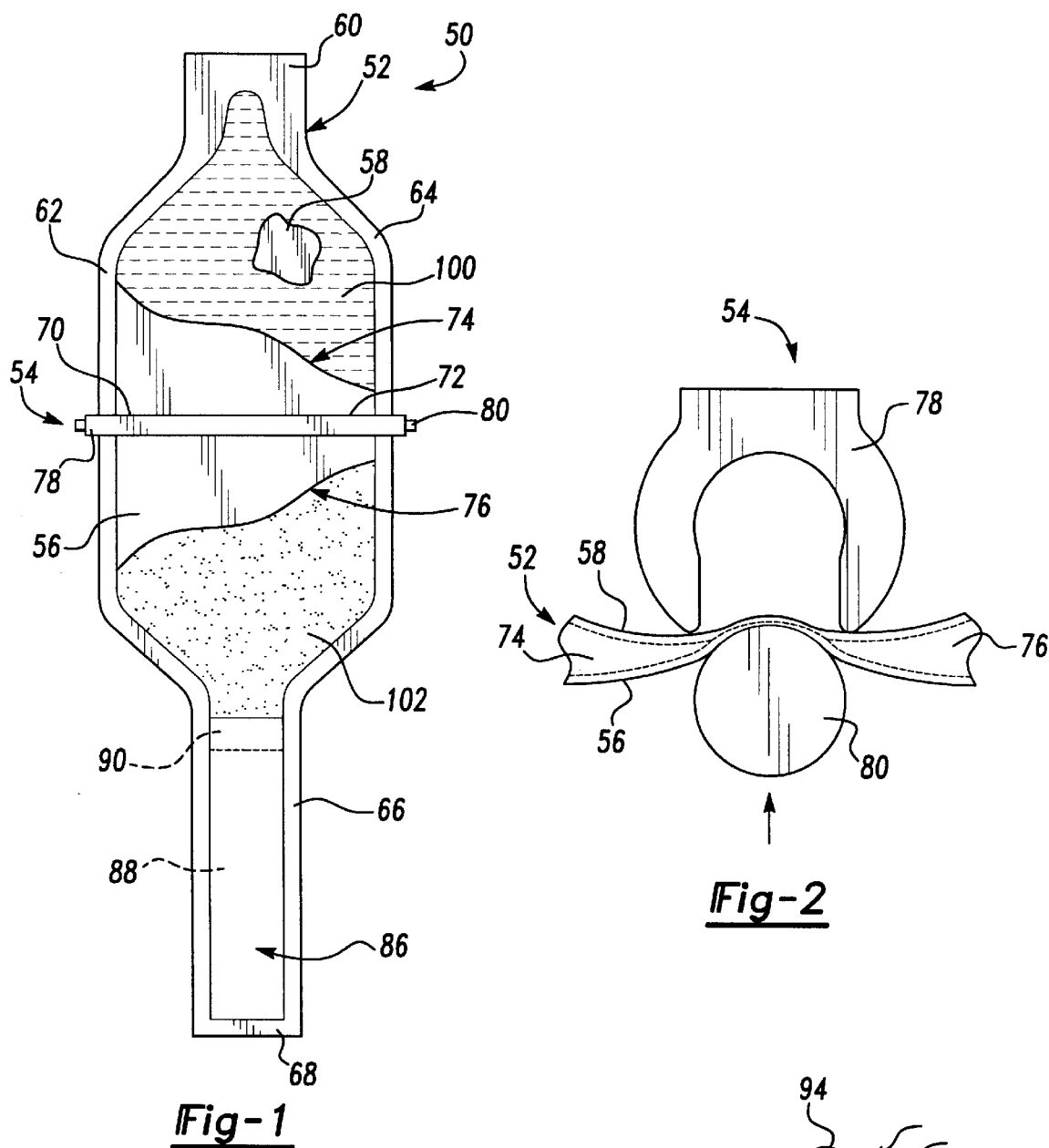
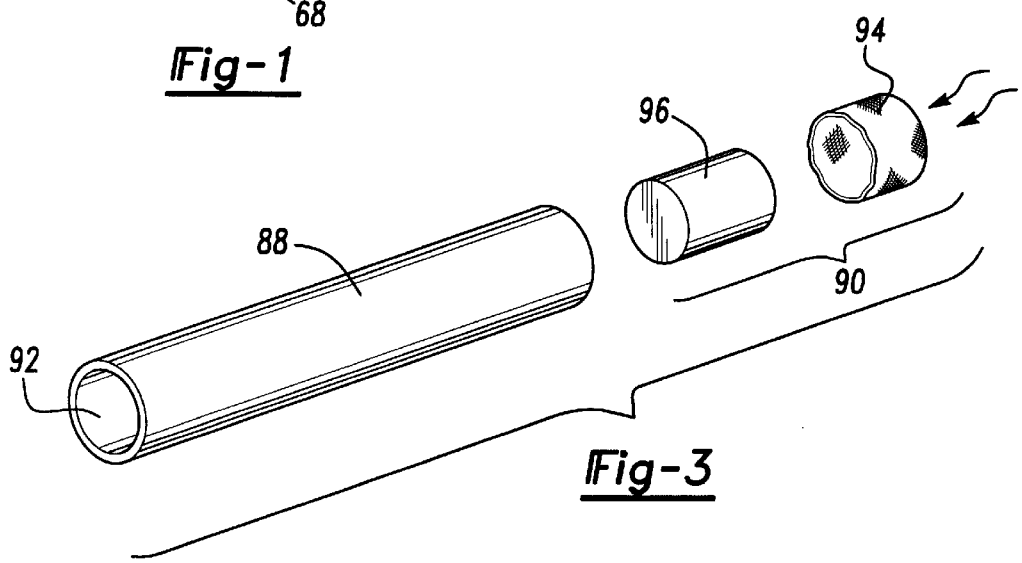

METHOD AND APPARATUS FOR MIXING A COMPOUND UTILIZING A GAS PERMEABLE BARRIER

TECHNICAL FIELD

The present invention relates generally to a process and a device for producing a mixed compound such as a sterile-packed bone cement and more particularly to a process and a device in which employs a barrier to eliminate or substantially reduce the amount of a liquid component of the compound that is drawn into a vacuum chamber.

BACKGROUND OF THE INVENTION

Background Art

The natural joints in the human body are often subject to degenerative changes resulting, inter alia, from disease or trauma. If these defects have progressed too far so as to be irreversible and untreatable, it is necessary to replace the natural joints or bones by corresponding implants. Examples of bone replacement materials that may be mentioned are shaped implants of a wide variety of kinds. For implementation, these bone replacement materials may be anchored in the natural bone using bone cements.

Customary bone cements are composed of a solid component, which consists of a finely divided acrylic polymer and of further additives, such as polymerization initiators, together if desired, with X-ray contrast media and colorants, and of a liquid component, which consists of an acrylic monomer and of further additives such as polymerization accelerators and stabilizers. The polymer powder component of cement consists preferably of granular particles with a spherical shape. The particle size preferably lies within a narrow range or is substantially uniform.

A device for combining the polymer powder and the liquid monomer in a sterile manner is disclosed in commonly assigned U.S. Pat. No. 5,370,221 entitled "Flexible Package for Bone Cement Components", the disclosure of which is hereby incorporated by reference as if fully set forth herein. In one embodiment, the device has a first chamber for the liquid monomer, a second chamber for the powdered polymer, a removable barrier between the first and second chambers, a vacuum chamber, and a filter. The vacuum chamber of this device is in fluid connection with the second chamber; the filter prevents the powdered polymer from entering the vacuum chamber. Removal of the barrier permits fluid communication between the first and second chambers. The vacuum in the vacuum chamber draws the liquid monomer through the powdered polymer, permitting the two components to be precisely mixed at a predetermined ratio in a sterile environment. While this device made a significant advance in the provision of sterile bone cements, further improvement in the area of vacuum mixing is desirable.

For example, in situations where the vacuum mixing devices have been stored for a large period of time, it has been demonstrated that the vacuum level in the vacuum chamber of some of these devices tends to decrease over a period of time. When vacuum mixing devices that have been stored for long periods of time are used, the vacuum chamber may not have a sufficient level of vacuum to cause the liquid monomer to fully wet all of the powdered polymer. In such cases, it is then necessary to manually mix the components by kneading the material in the container.

One solution suggested to increase the shelf life of the device relates to an increased amount of vacuum by either enlarging the vacuum chamber or increasing the magnitude of the vacuum. However, if the level of vacuum is too great, a portion of the liquid monomer tends to be drawn completely through the powdered polymer and into the vacuum reservoir. In such situations, the powdered polymer and the liquid monomer are not mixed at their proper ratio.

SUMMARY OF THE INVENTION

A general object of the present invention is to provide a container for a mixing a compound having a liquid component utilizing differential pressure.

A more specific object of the present invention is to provide a device for producing a sterile-packed bone cement which utilizes differential pressure to mix a liquid monomer and a solid polymer and which has a relatively long shelf life.

It is another object of the present invention to provide a device for producing a sterile-packed bone cement which utilizes a barrier to permit passage of a gas but resist infiltration of a liquid component of the bone cement into the vacuum chamber.

It is a further object of the present invention to provide a method for producing a sterile-packed bone cement which utilizes differential pressure to mix a liquid monomer and a solid polymer and which has a relatively long shelf life.

In one form, the present invention provides a container for first and second components that are to be mixed within the container with the container including:

a divider for dividing the container into first and second compartments for isolating the first component from the second compartment, the first compartment containing the liquid component and the second compartment containing the powder component;

a vacuum source in fluid communication with the second compartment, the vacuum source being of sufficient size to draw the first component through the second component to thereby ensure thorough admixing of the first and second components after the integrity of the divider is compromised; and a barrier mechanism disposed between the second compartment and the vacuum reservoir, the barrier mechanism forming a barrier that permits passage of a gas but resists infiltration of the first component into the vacuum source.

In a more specific form, the present invention provides a device for producing a sterile-packed bone cement having a relatively long shelf life, which comprises:

a divider for dividing the container into first and second compartments for isolating the components from one another, the first compartment containing the liquid component and the second compartment containing the powder component;

a vacuum source in fluid communication with the second compartment, the vacuum source being of sufficient size to ensure take up of substantially all residual interstitial gasses to thereby ensure thorough admixing of the liquid and powder components after the integrity of the divider is compromised; and a barrier mechanism disposed between the second compartment and the vacuum source, the barrier mechanism forming a barrier to resist infiltration of the liquid component into the vacuum source but permit passage of a gas.

In yet another form, the present invention provides a method for forming bone cement comprising the steps of:

providing a container having first and second compartments and a vacuum chamber, the first compartment being filled with a liquid component, the second compartment being filled with powder component and isolated from the first compartment, the vacuum chamber having a negative pressure and being in fluid communication with the second compartment;

causing the first and second compartments to be in fluid communication with one another to thereby permit the vacuum chamber to draw the liquid component into the second chamber;

interposing a barrier mechanism having a gas permeable barrier between the vacuum chamber and the second compartment, the gas permeable barrier resisting penetration by the liquid component; and admixing the liquid component and powder component under vacuum pressure.

BRIEF DESCRIPTION OF THE DRAWINGS

Additional advantages and features of the present invention will become apparent from the subsequent description and the appended claims, taken in conjunction with the accompanying drawings, wherein:

FIG. 1 is a diagrammatic sectional view showing a container constructed in accordance with a preferred embodiment of the present invention;

FIG. 2 is a side view of a portion of the container of FIG. 1 illustrating the temporary sealing device in greater detail;

FIG. 3 is an exploded perspective view of a portion of the container of FIG. 1, illustrating the barrier mechanism in greater detail.

DETAILED DESCRIPTION OF THE PREFERRED EMBODIMENT

Figure 4A:
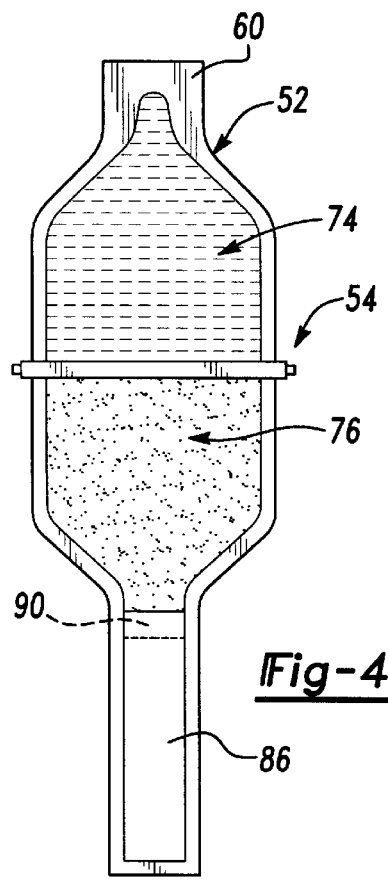
FIGS. 4A through 4F are diagrammatic sectional views illustrating operation steps of the mixing of a bone cement using the container of FIG. 1.

Referring now to the drawings in which like reference numerals designate like or corresponding parts throughout the several views, there is shown in FIG. 1 a packaging system for bone cement which is designated by reference numeral 50. Although the particular packaging system illustrated and discussed relates to a packaging system for bone cement, it will be understood that the teachings of the present invention have applicability to the packaging of other materials that may be combined through use of vacuum pressure. As such, the scope of the present invention will not be limited to applications involving bone cement but will extend to any other applications that employ vacuum pressure to admix a liquid component with another component or components.

The packaging system 50 includes a flexible container 52 and a divider 54. The flexible container 52 comprises a front panel 56 and a rear panel 58, each made of a thin generally impervious flexible film which is more fully described below. In the particular embodiment shown, the panels 56 and 58 are each formed from a single sheet of flexible film sealed to each other at a bottom edge 60 and side edges 62 and 64. The flexible container 52 further includes an extension 66 which is initially formed as a flattened tubular portion that is sealed on its edges 68 similar to edges 60, 62 and 64.

The divider 54 is arranged to provide a temporary seal of the inner surfaces of the panels 56 and 58 to each other along a line extending from an initial point 70 on the sealed edge 62 to a terminal point 72 on the sealed edge 64 to form a first compartment 74 and a second compartment 76. As will be appreciated by those skilled in the art, the divider 54 is initially placed on the flexible container 52 and the first and second compartments 74 and 76 are filled with a liquid component and a powder component of the bone cement, respectively. In the particular embodiment illustrated, the first compartment 74 is filled with a liquid monomer and the second compartment is filled with a powdered polymer.

The divider 54 comprises a C-shaped c lamp or outer retention member 78 and a cylindrical inner retention member 80 which fits within the hollow of the C-shaped outer retention member 78. When the divider 54 is assembled with respect to the flexible container 52 as shown in FIG. 2, the outer retention member 78 is positioned on the outside of the rear panel 58 and the inner retention member 80 is positioned on the outside of the front panel 56 such that the panels 56 and 58 are pinched together along a pair of parallel lines extending from the initial point 70 to the terminal point 72. The inner retention member 80 has a contoured upper end which fits within the inner hollow of outer retention member 78 and has a thickness substantially equal to the inner distance between the open ends of the C-shaped section of the outside retention member 78 so that a couple thickness of panels 56 and 58 is tightly compressed along a pair of parallel lines to form an effective seal between the first and second compartments 74 and 76. The outer retention member 78 is made of a resilient material so that the inner retention member 80 may be forced into position therein by placing it over the entire length of the opening of the outer retention member 78 and then pressing it into place. Inner retention member 80 has a contoured upper end which can open the open ends of the C-shaped section of the outside retention member 78 to accommodate the inner retention member 80.

Both the outer retention member 78 and the inner retention member 80 are long enough to reach from the initial point 70 to the terminal point 72. Preferably, the inner retention member 78 is somewhat longer than the outer retention member 78 to provide for a gripping point when the retention members 78 and 80 are to be separated and removed when compromising the integrity of the divider 54 to permit the first and second compartments 74 and 76 to be brought into fluid communication with one another.

Disposed adjacent the second compartment 76 is a vacuum reservoir 86. In the embodiment illustrated, the vacuum reservoir 86 comprises a cylindrical polyethylene tube 88 closed at its end adjacent second compartment 76 by barrier mechanism 90. Barrier mechanism 90 permits the passage of air through the tube interior 92 of the cylindrical polyethylene tube 88 as will be discussed in detail, below. It should be understood that the vacuum reservoir 86 can comprise a separate vacuum cylinder, having a frangible opening, which permits the user to break the cylinder opening just prior to use. When such an approach is used, the flexible container 52 does not have to be placed under vacuum when the flexible container 52 is initially filled with the liquid and the powder components. For example, the divider 54 would isolate the liquid and powder components in the compartments 74 and 74 and the vacuum reservoir 86 would be heat sealed into position in the extension 66 without a vacuum being drawn in the second compartment 76. When the user is ready to prepare the bone cement, the frangible seal of the vacuum reservoir 86 would be broken, such as by a twisting motion, thereby reducing the pressure in the second compartment 76. The vacuum reservoir 86 would be configured to have a volume sufficiently large to hold, under reduced pressure, the air from the second compartment 76, as well as the residual air that will be displaced from the powder component by the liquid component upon removal of the divider 54.

In FIG. 3, the barrier mechanism 90 is illustrated in greater detail. The barrier mechanism 90 is shown to include a barrier member 94 and a plug member 96. The barrier member 94 is formed from a gas permeable material that is positioned within the tube 88. Preferably, the barrier member 94 is inert relative to the liquid and powder components, as well as the bone cement. The barrier member 94 and the tube 88 cooperate to permit gasses to pass between the second compartment 76 and the vacuum reservoir 86 but form a barrier that is resistant to infiltration/penetration by the liquid and powder components. In selecting a material from which to make barrier member 94, it is critical that the material be resistant to infiltration/penetration by the liquid component, as opposed to being completely impervious to it at all pressures. However, the barrier member 94 is preferably formed from a material that is impervious to infiltration/penetration by the liquid component at the range of differential pressures that are exerted across the barrier member 94.

Those skilled in the art will understand that several factors must be considered and balanced prior to selecting a material for the barrier member 94. These factors include the surface tension of the liquid component, the range of differential pressures that are to be exerted onto the liquid component, and the surface energy, porosity and maximum pore size of the proposed material from which the barrier member 94 is to be made (the proposed material). It is critical to the invention that the proposed material be matched to the liquid component to ensure that the surface of the material does not wet-out when it is placed in contact with the liquid component. Accordingly, it is highly desirable to select a material having a low surface energy, such as those materials that are known in the art as being oleophobic.

To maximize per formance, it is desirable that the proposed material be highly porous and that the pores be sized as large as possible to permit gasses to be drawn through the barrier member 94 as rapidly as possible. However, the maximum pore size should be small enough so that the material resists penetration by the liquid component over the range of differential pressures that are expected to be exerted onto the liquid component.

Testing has shown that when a liquid that includes methylmethacrylate is used as the liquid component, good results have been obtained with highly porous oleophobic materials having maximum pore sizes of about 3 microns in diameter, with the preferred maximum pore size being about 1 micron in diameter. When exposed to a minimum differential pressure of about 2 pounds per square inch to a differential pressure of about 9 pounds per square inch, these materials provide good results both in terms of their ability to resist penetration by the liquid component as well as in the overall rate with which gasses are transmitted through the barrier member 94. One material tested with particularly good success has been a GORE-TEX RST® laminate manufactured by W. L. Gore and Associates, Inc.

In the particular embodiment illustrated, the plug member 96 is lodged in the tube 88 and supports the barrier member 94 to prevent the barrier member 94 from collapsing or displacing due to the pressure differential between second compartment 76 and the vacuum reservoir 86. The plug member 96 is preferably constructed in a highly porous manner to minimize pressure losses across barrier mechanism 90. The plug member 96 may be formed from cotton or another textile. Preferably, the plug member 96 is fabricated from an olefinic material, having a generally cylindrical shape with a plurality of pores formed therethrough.

In the embodiment illustrated, the barrier member 94 is sufficiently sized to cover the end of the plug member 96 and overlap its sides. The barrier member 94 and plug member 96 are then inserted into the end of the tube 88 and pushed forwardly toward the end of the tube that will be adjacent to the second compartment 76. Construction in this manner ensures the formation of a perimeter seal around the inner diameter of the tube 88 that will prevent the liquid monomer from migrating around the barrier member 94 and into the vacuum reservoir 86. Those skilled in the art will understand, however, that other methods may be employed to prevent the liquid monomer from traversing the barrier member 94 to penetrate into the vacuum reservoir 86. Those skilled in the art will also understand that the extension 66 must also be sized and shaped to prevent the liquid monomer from traversing around the tube 88 and into the extension 66. In this regard, the extension 66 is sized and shaped so as to ensure that liquid monomer passing through the powdered polymer is directed against the barrier member 94. Alternatively, a seal (not shown) may be placed around the circumference of the vacuum reservoir 86 to prevent the liquid monomer from entering the extension 66.

The method of operation using the packaging system 50 according to a preferred embodiment of the present invention is shown in FIGS. 4A through 4E. In FIG. 4A, the container 52 is shown with the first compartment 74 being filled with a liquid component 100 and the second compartment 76 being filled with a powdered component 102. The liquid component 100 may be a methyl methacrylate monomer containing an amine accelerator and the powdered component 102 may be a poly methyl methacrylate and a copolymer of methyl methacrylate and styrene, together with benzoyl peroxide and barium sulphate. An antibiotic material may also be combined with the liquid component 100 or the powdered component 102.

The vacuum reservoir 86 is initially placed in the extension 66 and the powdered component 102 is placed within the second compartment 76. Thereafter a vacuum is drawn on the extension 66 such that the interior of the extension 66 and the second compartment 76 are maintained in a substantially airless state. The nozzle is then heat sealed at the edge 68 while the vacuum is maintained inside the second compartment 76 and the extension 66. The liquid component 100 is then placed in the first compartment 74 in a similar manner to that described above and then the second compartment 74 is sealed. Care is taken so that little, if any, air enters the first compartment 74 while the first compartment 74 is being filled with the liquid component 100. The resulting structure of the packaging system 50 is that which is shown in FIG. 1.

Figure 4B:
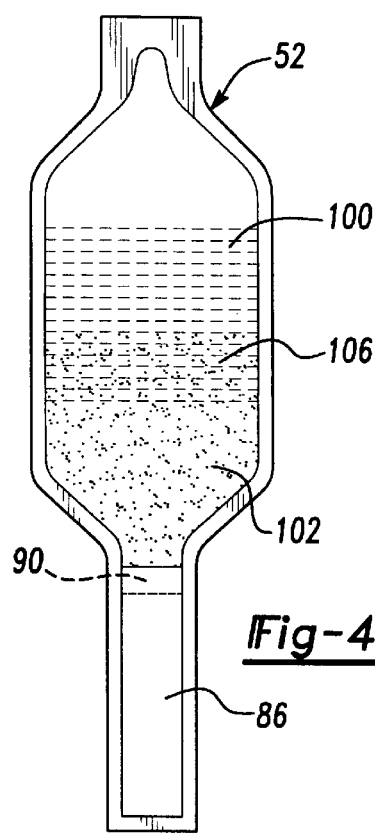
Figure 4C:
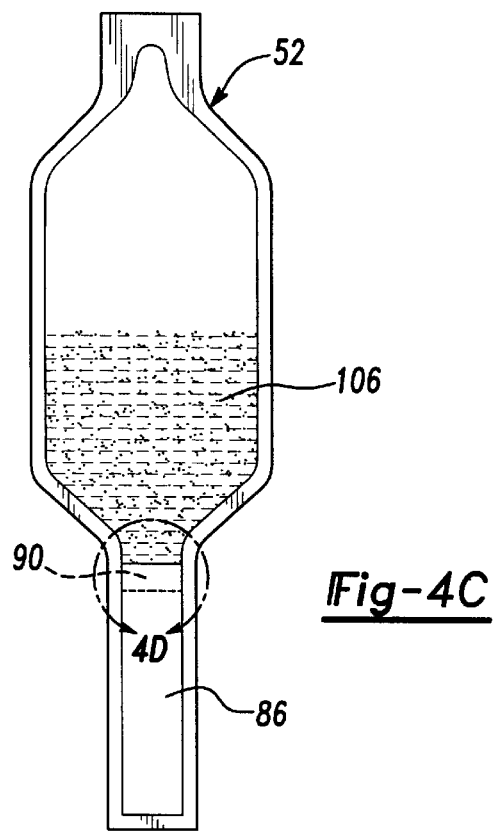
Figure 4D:
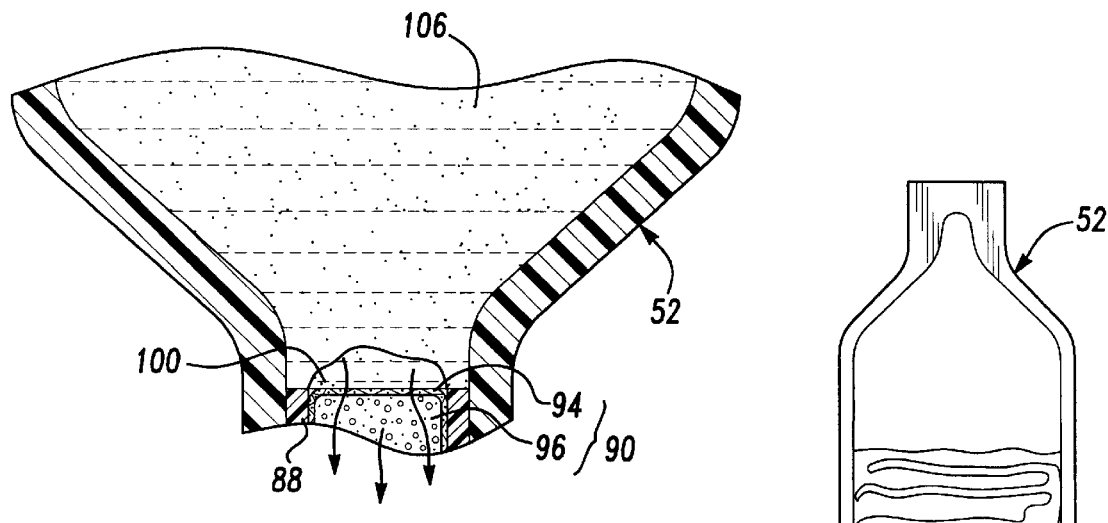

FIG. 4B shows the container 52 shortly after the divider 54 has been removed and the liquid component 100 has started to wet the powdered component 102 so as to form bone cement represented by the area 106. The liquid component 100 is driven towards and into the powdered component 102 by the atmospheric pressure acting on the first compartment 74 containing the liquid component 100. The residual air in the interstitial voids between the particles of the powdered component 102 is drawn through the barrier mechanism 90 and into the vacuum reservoir 86. In FIG. 4C, the in situ wetting of the liquid component 84 into the powdered component 102 is complete. All of the interstitial voids between the particles of the powdered component 102 are filled by the liquid component 100 and the residual air is held inside the vacuum reservoir 86 at a partial vacuum. Accordingly, little if any manipulation of the container 52 is required to mix the bone cement 106. In FIG. 4D, the portion of the liquid component 100 that is drawn completely through the powdered component 102 is shown to contact the barrier member 94 which resists infiltration of the liquid component 100 into the vacuum reservoir 86. The arrows in FIG. 4D depict gasses passing through the barrier mechanism 90 into the vacuum reservoir 86.

Preferably, the vacuum reservoir 86 and the barrier member 94 cooperate to permit a minimum differential pressure of about 2 pounds per square inch to be exerted on the liquid component 100 upon removal of the divider 54 so that substantially all residual interstitial gasses are taken up and the liquid component 100 drawn through and wetting the powder component 102 within about 5 seconds to about 60 seconds after the divider 54 has been released. More preferably, the vacuum reservoir 86 and the barrier member 94 cooperate to permit substantially all residual interstitial gasses to be taken up and the liquid component 100 drawn through the powder component 102 within about 10 seconds to about 30 seconds after the divider 54 has been released when a differential pressure of about 2 pounds per square inch is exerted onto the liquid component 100.

Figure 4E:
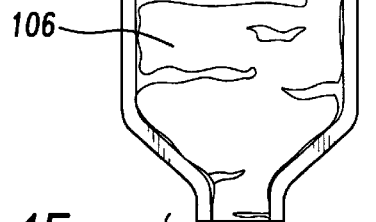
Figure 4F:
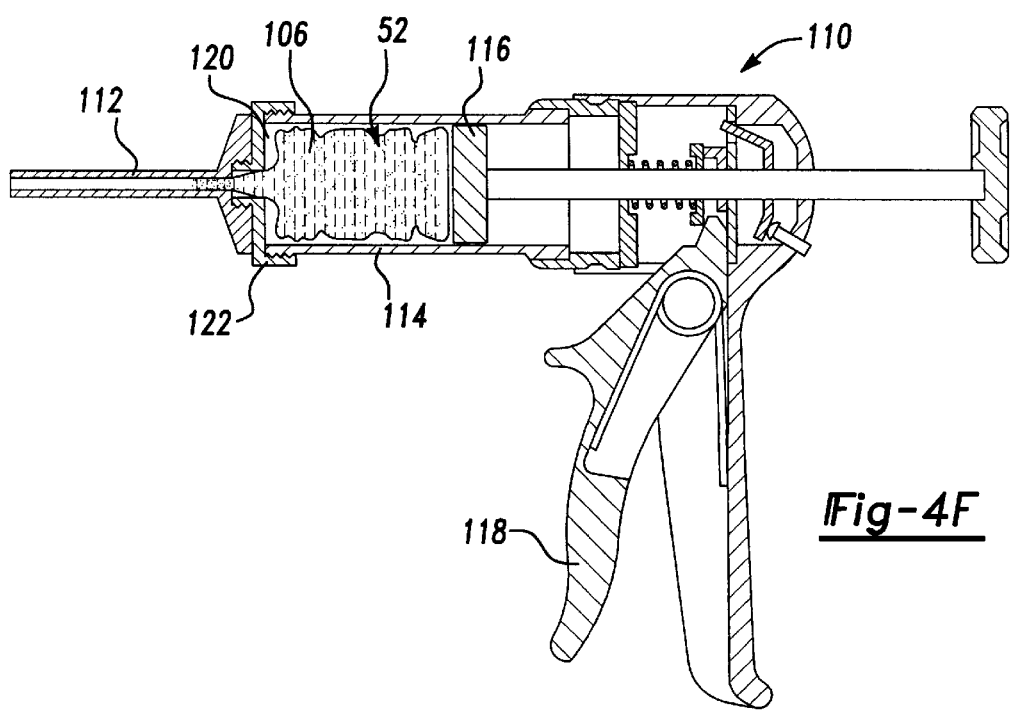

The bone cement 106 within the container 52 may then be dispensed in the manner shown in FIGS. 4E and 4F. The container 52 is placed within a bone cement syringe 114 with the extension 66 passing through the open end 120 of the bone cement syringe 114. The extension 66 is passed through a cap 122 and the cap 122 is threadably coupled to the bone cement syringe 114. At least a portion of the extension 66 is severed and the vacuum reservoir 86 is removed. A tubular nozzle 112 is then coupled to the cap 122. The plunger 116 of the bone cement gun 110 is then displaced toward the flexible container 52 by manipulation of the activation member 118 of the bone cement gun 110. As the plunger 116 compresses the flexible container 52, bone cement 116 is delivered through the tubular member 12. By choice of suitable material, the flexible container 52 can be fully compressed, leaving only a small fraction of bone cement inside the flexible container 52.

Figure 5:
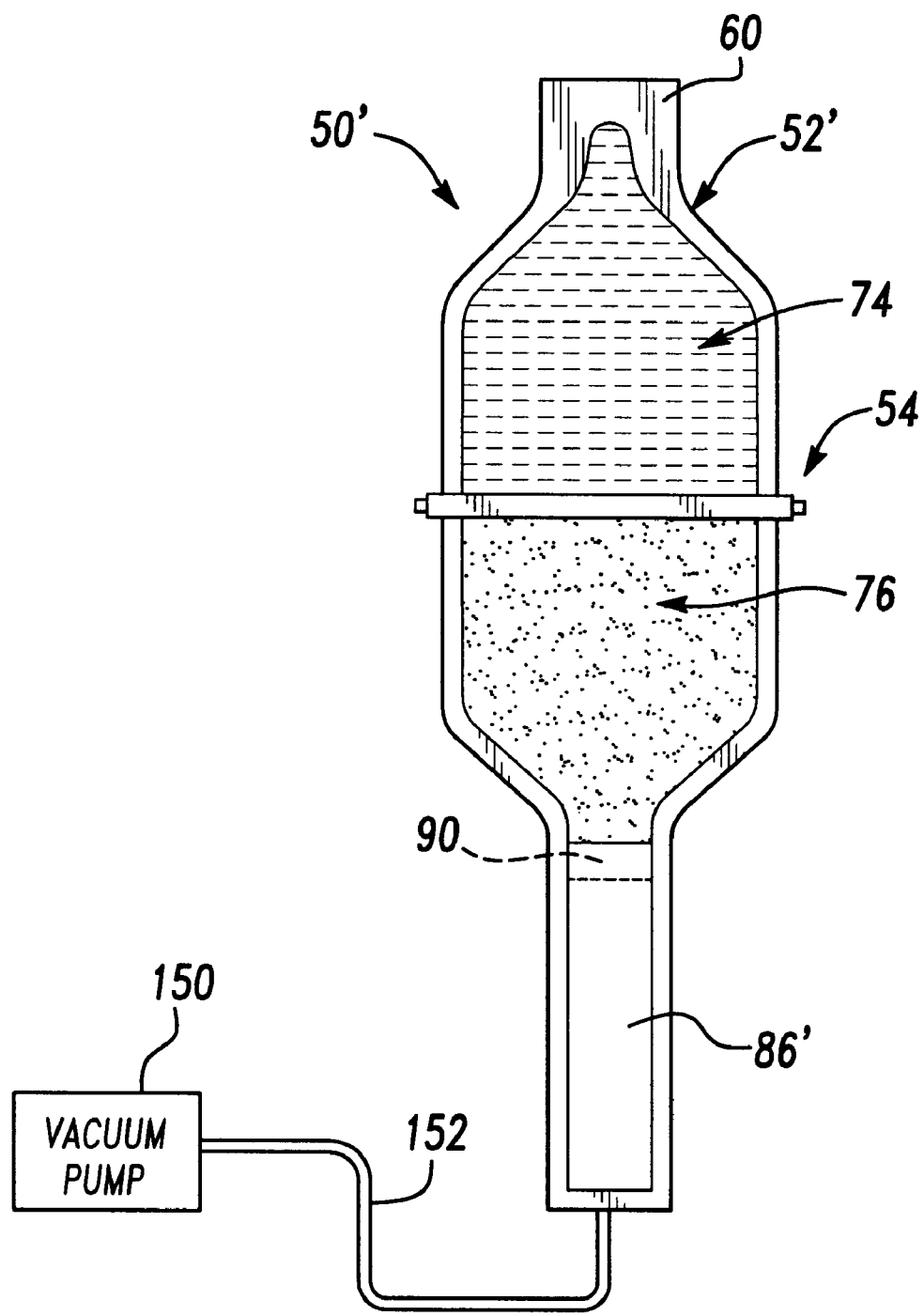
FIG. 5 is a view showing the container connected to a vacuum pump.

While the packaging system 50 has been described thus far as employing a vacuum reservoir 86, those skilled in the art will appreciate that the invention, in its broader aspects, may be constructed somewhat differently. For example, the packaging system may be formed to include a vent port 86' as shown in FIG. 5. In this arrangement, container 52' is substantially similar to container 52 except that container 52' includes a vent port 86' rather than a vacuum reservoir 86. In the embodiment illustrated, vent port 86' includes a tube 88, a barrier mechanism 90 having a barrier member 94 and a plug member 96. Vent port 86' is not charged with vacuum pressure prior to the use of container 52'. In operation, a vacuum pump 150 is coupled to the vent port 86' via a vacuum hose 152. Upon the release of the divider 54, the vacuum pump 150 and the barrier member 94 cooperate to permit a differential pressure to be exerted on the liquid component which causes the liquid component to be drawn through a porous or powder component in the second compartment 76'. Alternatively, an externally initiated force may be applied to the first compartment 74' to create a pressure differential to cause the liquid component to be displaced into the porous or powder component in the second compartment 76'.

As another example, the divider 54 may be formed as an integral (i.e., non-removable) barrier between the first and second compartments 74 and 76. An example of this construction is disclosed in U.S. Pat. No. 5,549,380 entitled "Mixing Device for Manufacturing Bone Cement", the disclosure of which is hereby incorporated by reference as if fully set forth herein. Accordingly, those skilled in the art will understand that the integrity of the divider 54 may be compromised by the removal of the divider, either in whole or in part, or by puncturing, rupturing, impacting, cutting, tearing, severing, or otherwise causing the divider to be opened to permit fluid communication between the first and second compartments 74 and 76.

As a further example, the first and second compartments 74 and 76 may be non-integral (i.e., separable) from one another. An example of this construction is disclosed in U.S. Pat. No. 5,852,241 entitled "Method and Device for Feeding Components for Bone Cement Into a Mixing Vessel for These", the disclosure of which is hereby incorporated by reference as if fully set forth herein. Accordingly, those skilled in the art will understand that the integral configuration of the container 52 wherein the first and second compartments 74 and 76 are permanently joined is merely exemplary and that the scope of the present invention will extend to containers where the first and second compartments are joined together prior to the mixing of the contents contained therein.

While the invention has been described in the specification and illustrated in the drawings with reference to a preferred embodiment, it will be understood by those skilled in the art that various changes may be made and equivalents may be substituted for elements thereof without departing from the scope of the invention as defined in the claims. In addition, many modifications may be made to adapt a particular situation or material to the teachings of the invention without departing from the essential scope thereof. Therefore, it is intended that the invention not be limited to the particular embodiment illustrated by the drawings and described in the specification as the best mode presently contemplated for carrying out this invention, but that the invention will include any embodiments falling within the foregoing description and the appended claims.

What is claimed is:

1. A container for packaging liquid and powder components that are to be mixed within the container, the container comprising:

a first compartment containing the liquid component;

a second compartment containing the powder component;

a divider isolating the first and second compartments;

a vacuum source in fluid communication with the second compartment, the vacuum source being of sufficient size and pressure to ensure take up of substantially all gasses in the first and second compartments to thereby ensure thorough admixing of the liquid and powder components after the integrity of the divider has been compromised and the first and second compartments have been brought into fluid communication with one another; and a barrier mechanism disposed between the second compartment and the vacuum source, the barrier mechanism including a porous membrane constructed from an oleophobic material, the barrier mechanism forming a barrier to resist infiltration of the liquid component but permit the gasses in the first and second compartments to pass into the vacuum source.

2. The container of claim 1, wherein the porous membrane is formed from a material having a low surface energy to prevent the liquid component from wetting out the surface of the barrier mechanism.

3. The container of claim 2, wherein the oleophobic material is expanded polytetrafluoroethylene.

4. The container of claim 1, wherein the barrier mechanism filter means further includes a plug member for supporting the porous membrane.

5. The container of claim 4, wherein the plug member is formed from an olefinic material.

6. The container of claim 1, wherein the porous membrane is inert relative to the liquid component and the powder component.

7. The container of claim 1, wherein the liquid component includes an acrylic monomer.

8. The container of claim 1, wherein the powder component includes a powdered acrylic polymer.

9. The container of claim 1, wherein the liquid and powder components are admixed to form a bone cement.

10. The container of claim 1, wherein the vacuum source is a vacuum reservoir.

11. The container of claim 1, wherein the vacuum source is a vacuum pump.

12. The container of claim 1, wherein the divider includes a clamp member and a retention member which cooperate to compress a first side of the container against a second side of the container to form a seal that divides the first and second compartments and wherein the divider is compromised by releasing the clamp and retention members from one another.

13. A container for packaging liquid and powder components that are to be mixed within the container, the container comprising:

a first compartment containing the liquid component;

a second compartment containing the powder component;

a divider isolating the first and second compartments;

a vacuum source in fluid communication with the second compartment, the vacuum source being of sufficient size and pressure to ensure take up of substantially all gasses in the first and second compartments to thereby ensure thorough admixing of the liquid and powder components after the integrity of the divider has been compromised and the first and second compartments have been brought into fluid communication with one another; and a gas permeable barrier disposed between the second compartment and the vacuum source, the gas permeable barrier including a porous membrane constructed from an oleophobic material, the porous membrane being resistant to penetration by the liquid component, the gas permeable barrier permitting the vacuum source to draw the liquid component into the second compartment after the divider has been compromised.

14. The container of claim 13, wherein after the divider has been compromised, the vacuum source and the gas permeable barrier cooperate such that a minimum differential pressure of about 2 pounds per square inch is exerted on the liquid component.

15. The container of claim 13, wherein after the divider has been compromised, the vacuum source and the gas permeable barrier cooperate to permit substantially all residual interstitial gasses to be taken up within about 5 seconds to about 60 seconds after the divider has been released.

16. The container of claim 15, wherein the vacuum source and the gas permeable barrier cooperate to permit substantially all residual interstitial gasses to be taken up within about 10 seconds to about 30 seconds after the divider has been compromised.

17. The container of claim 13, wherein the gas permeable barrier is impervious to the liquid component when a differential pressure of about 2 pounds per square inch is exerted onto the liquid component.

18. The container of claim 17, wherein the gas permeable barrier is impervious to the liquid component when a differential pressure of about 9 pounds per square inch is exerted onto the liquid component.

19. The container of claim 13, wherein the liquid and powder components are admixed to form a bone cement.

20. The container of claim 15, wherein the vacuum source is a vacuum reservoir.

21. The container of claim 13, wherein the vacuum source is a vacuum pump.

22. The container of claim 13, wherein the divider includes a clamp member and a retention member which cooperate to compress a first side of the container against a second side of the container to form a seal that divides the first and second compartments and wherein the divider is compromised by releasing the clamp and retention members from one another.

23. A container for packaging liquid and powder components that are to be mixed within the container, the container comprising:

a first compartment containing the liquid component;

a second compartment containing the powder component;

a divider isolating the first and second compartments;

a vacuum source in fluid communication with the second compartment, the vacuum source being of sufficient size and pressure to ensure take up of substantially all gasses in the first and second compartments to thereby ensure thorough admixing of the liquid and powder components after the integrity of the divider has been compromised and the first and second compartments have been brought into fluid communication with one another; and a barrier mechanism disposed between the second compartment and the vacuum source, the barrier mechanism having a barrier member that is formed from an oleophobic material and which includes a plurality of pores, the plurality of pores being generally sized to resist transmission of the liquid component through the barrier mechanism, the plurality of pores also being generally sized to permit fluid communication of residual interstitial gasses in the second compartment, the barrier mechanism permitting the vacuum source to draw the liquid component into the second compartment after the divider has been compromised.

24. The container of claim 23, wherein each of the plurality of pores has a maximum diameter of about 1 micron.

25. The container of claim 23, wherein the liquid and powder components are admixed to form a bone cement.

26. The container of claim 23, wherein the vacuum source is a vacuum reservoir.

27. The container of claim 23, wherein the vacuum source is a vacuum pump.

28. The container of claim 23, wherein the divider includes a clamp member and a retention member which cooperate to compress a first side of the container against a second side of the container to form a seal that divides the first and second compartments and wherein the divider is compromised by releasing the clamp and retention members from one another.

29. A container for packaging liquid and powder components that are to be mixed within the container, the container comprising:

dividing means for isolating a first compartment of the container from a second compartment of the container, the first compartment containing the first component and the second compartment containing the second component;

vent means in fluid communication with the second compartment;

differential pressure means for exerting a differential pressure on the liquid component to take up substantially all residual interstitial gasses to thereby ensure thorough admixing of the liquid and powder components upon release of the dividing means; and barrier means disposed between the second compartment and the vent means, the barrier means including a porous membrane that is formed from an oleophobic material, the barrier means forming a barrier to resist infiltration of the liquid component into the vent means.

30. The container of claim 29, wherein the differential pressure means includes a source of vacuum pressure.

31. The container of claim 29, wherein the liquid and powder components are admixed to form a bone cement.

32. A method for admixing a compound comprising the steps of:

providing a container having first and second compartments, the first compartment being filled with a liquid component, the second compartment being filled with powder component and isolated from the first compartment;

coupling a vacuum source having a vacuum pressure to the second compartment such that the vacuum source is in fluid communication with the second compartment;

causing the first and second compartments to be in fluid communication with one another to thereby permit a differential pressure created by the vacuum source to force the liquid component into the second chamber;

interposing a barrier mechanism having a gas permeable barrier that is formed from a porous oleophobic material between the vacuum source and the second compartment, the gas permeable barrier resisting penetration by the liquid component; and admixing the liquid component and powder component under vacuum pressure.

33. The method of claim 32, wherein the compound is a bone cement.

* * * * *

UNITED STATES PATENT AND TRADEMARK OFFICE
CERTIFICATE OF CORRECTION

PATENT NO.    : 6,286,670 B1                                           Page 1 of 1
DATED         : September 11, 2001
INVENTOR(S)   : Daniel B. Smith It is certified that error appears in the above-identified patent and that said Letters Patent is hereby corrected as shown below:

<u>Column 1,</u>
Line 9, delete "in".

<u>Column 2,</u>
Line 10, delete "a".

<u>Column 4,</u>
Line 11, "c lamp" should be -- clamp --.
Line 61, second occurrence of "74" should be -- 76 --.

<u>Column 5,</u>
Line 41, "per formance" should be -- performance --.

<u>Column 6,</u>
Line 52, "74" should be -- 76 --.

<u>Column 7,</u>
Line 42, "12" should be -- 112 --.

<u>Column 10,</u>
Line 13, "claim 15" should be -- claim 13 --.

Signed and Sealed this

Eighth Day of October, 2002

*Attest:*

*Attesting Officer*

JAMES E. ROGAN
*Director of the United States Patent and Trademark Office*